United States Patent [19]

Swallow et al.

[11] Patent Number: 4,502,301
[45] Date of Patent: Mar. 5, 1985

[54] SUPPORT STOCKING PRODUCT OR THE LIKE

[75] Inventors: Roger T. Swallow, Asheboro; William R. Jackson, Raleigh; Jack D. Pierce, Asheboro, all of N.C.

[73] Assignee: Rampon Products, Inc., Asheboro, N.C.

[21] Appl. No.: 428,111

[22] Filed: Sep. 29, 1982

[51] Int. Cl.³ .............................................. D04B 9/52
[52] U.S. Cl. ................................... 66/178 A; 128/165
[58] Field of Search .................. 66/178 A; 128/80 R, 128/165

[56] References Cited

U.S. PATENT DOCUMENTS 2,574,873 11/1951 Jobst ..................................... 128/165
2,816,361 12/1957 Jobst ................................. 128/165 X
3,889,494 6/1975 Patience et al. .................. 66/178 A

FOREIGN PATENT DOCUMENTS 165434 9/1955 Australia ............................. 128/165

Primary Examiner—Wm. Carter Reynolds
Attorney, Agent, or Firm—B. B. Olive

[57] ABSTRACT

An improved support stocking exhibits a compression profile customized to the patient's needs and corresponding to a computer program determined profile.

4 Claims, 34 Drawing Figures

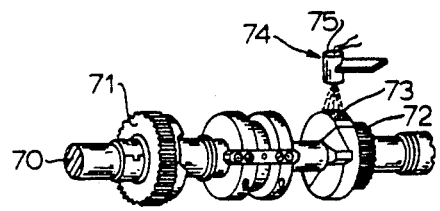
FIG. 15
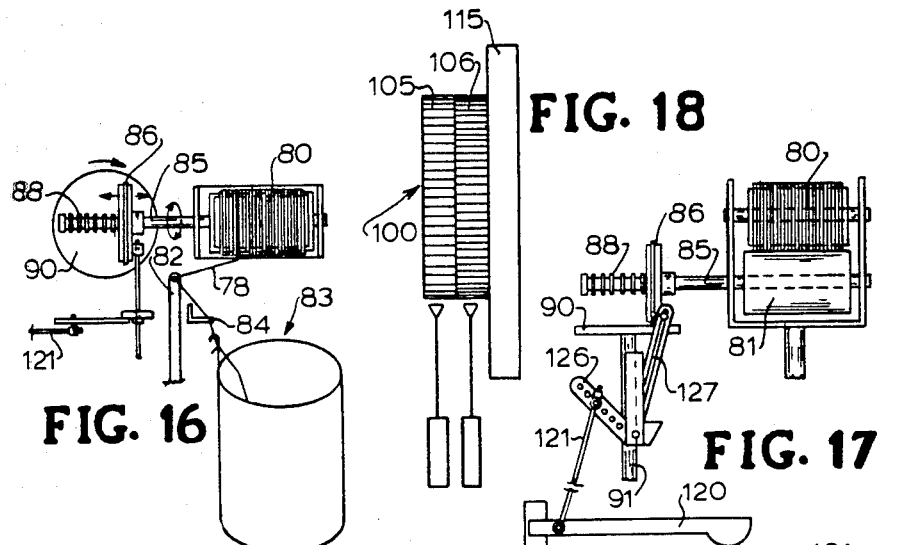
FIG. 18
FIG. 16
FIG. 17
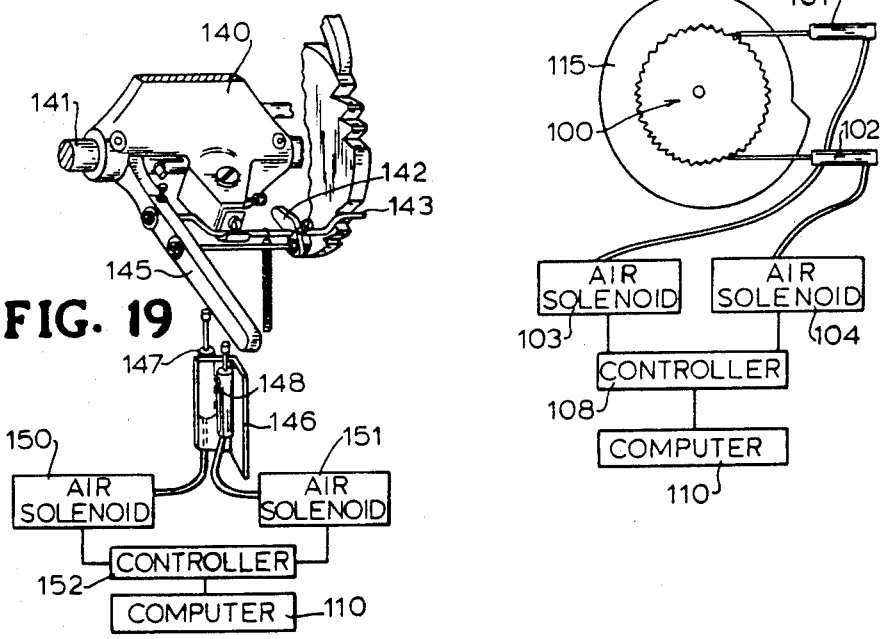
FIG. 19

SUPPORT STOCKING PRODUCT OR THE LIKE

CROSS-REFERENCE TO RELATED COPENDING APPLICATIONS

This application relates to the subject matter of separately-filed copending applications Ser. No. 427,911, filed Sept. 29, 1982, entitled "Program-Controlled Knitting Machine, Method and Products Thereof", and now-abandoned application Ser. No. 427,912, filed Sept. 29, 1982, entitled "Measuring Information Tape and Method for Support Stocking".

TECHNICAL FIELD

The invention relates to circular knit goods, particularly compressive stockings, and the like, for therapeutic use.

Background Art

While the invention is regarded as having application to goods other than compressive stockings, the provision of an improved compressive stocking construction is used as an illustrative example of how the invention is applied. The background art is thus explained with this example in mind.

It has long been known that elastic support stockings provide effective treatment for various chronic venous insufficiencies. In some instances, the patient can be fitted with immediately-available, ready-made hosiery. However, because of the wide range of leg lengths and sizes, some patients require elastic support stockings made to a specific prescription for the patient's individual requirements.

One conventional method for making a compressive stocking according to a specific patient prescription involves measuring the patient's limb to be fitted at various locations along the length of the limb, cutting a piece of flat elastic fabric to conform to the patient's specific limb dimensions and then completing the stocking by joining the edges into a longitudinal seam. U.S. Pat. No. 2,816,361 describes such a method for cutting an elastic fabric blank corresponding to the dimensions of a specific patient recorded on a special tape device and then seaming the blank at the edges to provide a compressive stocking corresponding to a particular patient's specific needs. U.S. Pat. No. 2,807,946 describes a method of making a shaped compressive stocking on a circular knitting machine by increasing and decreasing the tension applied to the elastic or so-called "rubber" feed during knitting. While the specific type of machine control contemplated in U.S. Pat. No. 2,807,946 is not described, it would be expected that such rubber feed tension control would be under mechanical control on the machine.

In view of the fact that the present product invention is preferably made in a program-controlled knitting operation it is also recognized that circular knitting machines have previously been operated under program control as distinct from use of a conventional pattern drum, or the like. For example, U.S. Pat. No. 3,069,881 teaches a punched card system with means to read the cards so as to control the knitting machine elements during the knitting sequence.

U.S. Pat. No. 3,232,079, in another example of a program-controlled circular knitting machine discloses a circular knitting machine in which program responsive electrical control means control various knitting elements, including raising and lowering the cylinder, to control the form of the circular knit fabric produced on the machine. However, this patent makes no suggestion or teaching for storing body, e.g., leg dimensions, or the like, for a specific patient and using this information in conjunction with known compressive characteristics obtainable from various machine settings also stored as a means for knitting a compressive stocking under program control to a specific prescription to obtain the construction of the present invention.

U.S. Pat. Nos. 3,670,527; 3,861,178; 3,866,442 and 4,018,064 further exemplify the state of the art with regard to program-controlled knitting machines.

Recognition is also given to the fact that storing of a specific size in memory and controlling a knitting machine to knit such size has been known. However, such machines do not provide for accommodation to a specific patient's needs nor do such machines progressively control both size and pressure.

With the above background art in mind, it becomes apparent that the art has not provided compressive stockings having a graduated pressure profile suited to the particular patient's limb dimensions and medical requirements and with a smooth, graduated transition in pressure from the ankle, through each leg segment point up to the gluteal furrow and with pressures determined so as to satisfy a physician-specified pressure profile based on the patient's needs. A critical analysis of compressive support stockings made according to the prior art reveals undesirable transitions in pressure. Also, the pressures do not correspond to the most desirable pressure profile and the profile is generally not precisely reproducible when a need for replacement occurs.

DISCLOSURE OF INVENTION

The invention provides compressive stockings or other therapeutic-type, tubular knit goods in which the size and amount of compression are fitted to the specific and graduated size of the patient's limb, the specific amount of compression and the specific pressure profile needed for the particular patient's medical condition.

Using compressive stockings as an example of the type of goods to which the invention is applied, the size and degree of graduated compression obtained in the invention product are preferably obtained by controlling selected machine elements under program control having access to a data bank in which information is stored relating some known predetermined number of combinations of machine settings to known and measured combinations of size and degree of compression. Using this prestored data, other data related to a patient's specific limb dimensions and a program for optimizing the selection of machine settings based on both sets of data, the desired stocking is knit and the desired graduated size and degree of compression are obtained by controlling the selected machine elements under program control.

In an illustrative embodiment of how the invention product may be made, the cylinder height and feed speed for the elastic thread, i.e., the so-called "rubber" feed, are the controlled machine elements. The first-mentioned set of data is obtained by knitting, insofar as is practicable, a set of sample tubes based on a selected number of possible cylinder height positions and a selected number of possible rubber feed positions. Not all of the possible machine setting combinations are knit since some of the possible cylinder height rubber feed combinations are impractical to knit. However, a sufficiently large number of samples are knit to provide a suitable data base from which optimal machine settings can be selected based on the input of additional data corresponding to the patient's particular limb size and the desired degree of compression corresponding to the limb profile. Combinations of graduated and uniform pressure profiles may be obtained.

While not part of the present invention, there is also illustrated a preferred method and measuring tape for recording the patient's physical limb size and desired degree of compression for data entry. The resulting compressive stocking product made according to the invention is believed to provide a novel construction exhibiting a degree of graduated compression and graduated size not heretofore obtained and thus provides a truly customized form of product.

DESCRIPTION OF THE DRAWINGS

FIGS. 3A–3F are fragmentary plan views representing collectively a composite plan view of the front side of a measuring information tape useful for recording the measurements taken according to FIG. 1 and FIGS. 5–7.

FIG. 15 is a fragmentary perspective view of a revolution sensor for a knitting machine useful in making the product of the invention.

FIG. 16 is a plan view of a rubber, i.e., elastic thread, feed control used in a knitting machine for making the product of the invention.

FIG. 17 is a side elevation view of the feed control of FIG. 16.

FIG. 18 is a top plan and somewhat schematic view of the linear lobe cam-gear control arrangement seen in FIG. 17.

FIG. 19 is a fragmentary perspective and schematic view of the main drum rack control used for positioning the elastic thread feed finger under program control in a knitting machine used for making the product of the invention.

BEST MODE FOR CARRYING OUT THE INVENTION

The product of the invention generally lends itself to any type of circular knit goods in which the goods, e.g., a compressive stocking, have either or both the size and degree of compression controlled along the length of the goods. Typical goods to which the invention is expected to be most widely applied are below-knee, above-knee, one-leg-leotard and leotard-type compressive stockings as illustrated in FIGS. 22–25 and in which control of both size and degree of compression are important. A lymphedeme sleeve for a mastectomy patient represents another anticipated application of the invention.

Broadly, as will be seen from later description, the invention makes possible customizing seamless tubular fabric goods to fit a specific body contour and with a specific compression profile fitted to such contour. While primarily directed to tubular seamless fabric goods made from circular knit elastic fabric, such as support stockings, the invention, as seen from later description, also lends itself to some extent to customizing tubular fabric goods formed from flat fabric.

For purposes of explaining the invention, it will be assumed for reference that there is a need for a single, thigh length, compressive stocking constructed according to the invention and graduated in both size and compression along the length of the stocking. To illustrate how this typical invention product may be made, the establishment, storing and use of the data to control the circular knitting of such a single compressive stocking will be explained as an example. From this explanation, it will be readily understood how other knit articles can be made according to the invention, such as those illustrated in FIGS. 22-25 and other circular knit tubular goods in which graduated size and compression are desirable features, particularly for therapeutic use.

Figure 2:
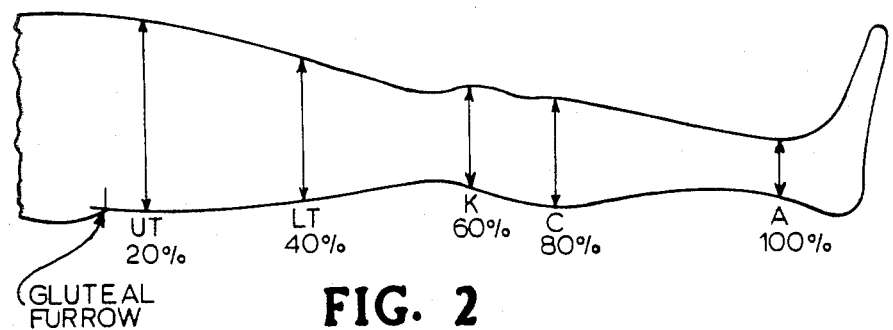
FIG. 2 is a pictorial view of the body portions of FIG. 1 in a supine position with an indication of a typical pressure profile at the points indicated in FIG. 1 using a selected point, the ankle point A being shown by way of example, as the reference point where 100% of the desired pressure is to be applied by way of further example.

In the compression stocking product being used by way of example of the invention product, the stocking is knit so as to provide a graduated pressure profile wherein the pressure exerted on the patient's limb is at a maximum, i.e., 100%, at a selected point, normally the ankle location, and decreases in proportion to the distance from the ankle as further illustrated in FIG. 2. While another reference point and another percentage, other than 100%, could be selected, the stated decrease in pressure from 100% at the ankle follows generally accepted recommendations based on clinical studies set forth in the medical literature or based on physician preference. It has been shown, for example, that certain pressure profiles built into a support stocking are effective in treating certain vascular disorders, including stasis ulcers, varicose veins and swelling of the limb. This form of medical treatment is called compression therapy. The compression therapy begins once a physician determines that a particular patient would benefit from this form of treatment.

It is necessary at the outset to achieve the desired stocking product of the invention that the physician or other trained technician collect accurate leg circumference data on the patient and also determine the pressure profile most beneficial to the patient. A description of this aspect of the invention is next explained.

Figure 1:
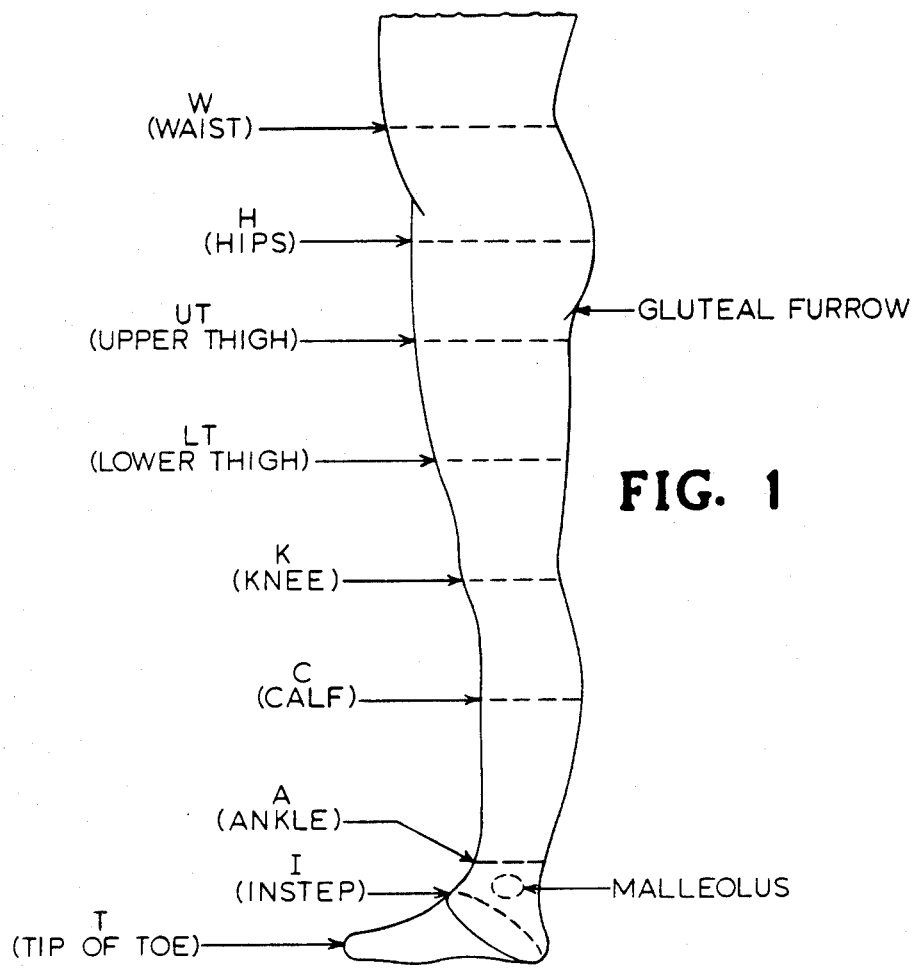
FIG. 1 is a pictorial view illustrating points on the foot, leg, thigh, et cetera, where measurements are taken in the supine position, as in FIG. 5, preparatory to knitting a compressive stocking according to the invention and corresponding to the particular measurements.
Figure 4:
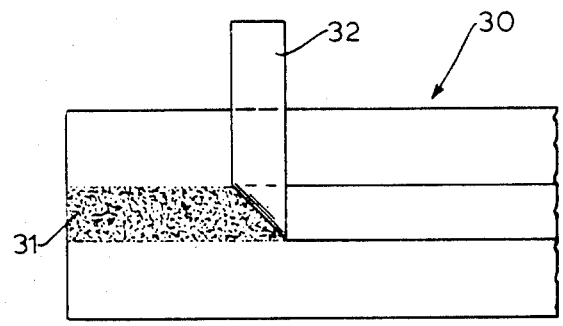
FIG. 4 is a fragmentary plan view of the back side of a portion of the measuring information tape tape shown in FIGS. 3A–3F showing an adhesive strip and removable cover strip provided for the length of the tape on the back side thereof.

As best illustrated in FIG. 1, various portions of the patient's limb and body are designated for reference with letter legends, as for examples W for the waist, H for the hips, UT for the upper thigh, and so forth as further seen in FIG. 1 and various measurements are taken with respect to these portions of the body as later discussed in reference to FIGS. 3A-3F and 5-8. To facilitate the taking and recording of measurements, there is provided a measuring information tape 30 having printed indicia on the front or face of the tape (FIGS. 3A-3F) and a strip of adhesive material 31 covered by a removable, narrow, paper strip 32 on the back and running lengthwise of the tape 30 (FIG. 4).

Figures 3A, 3B:
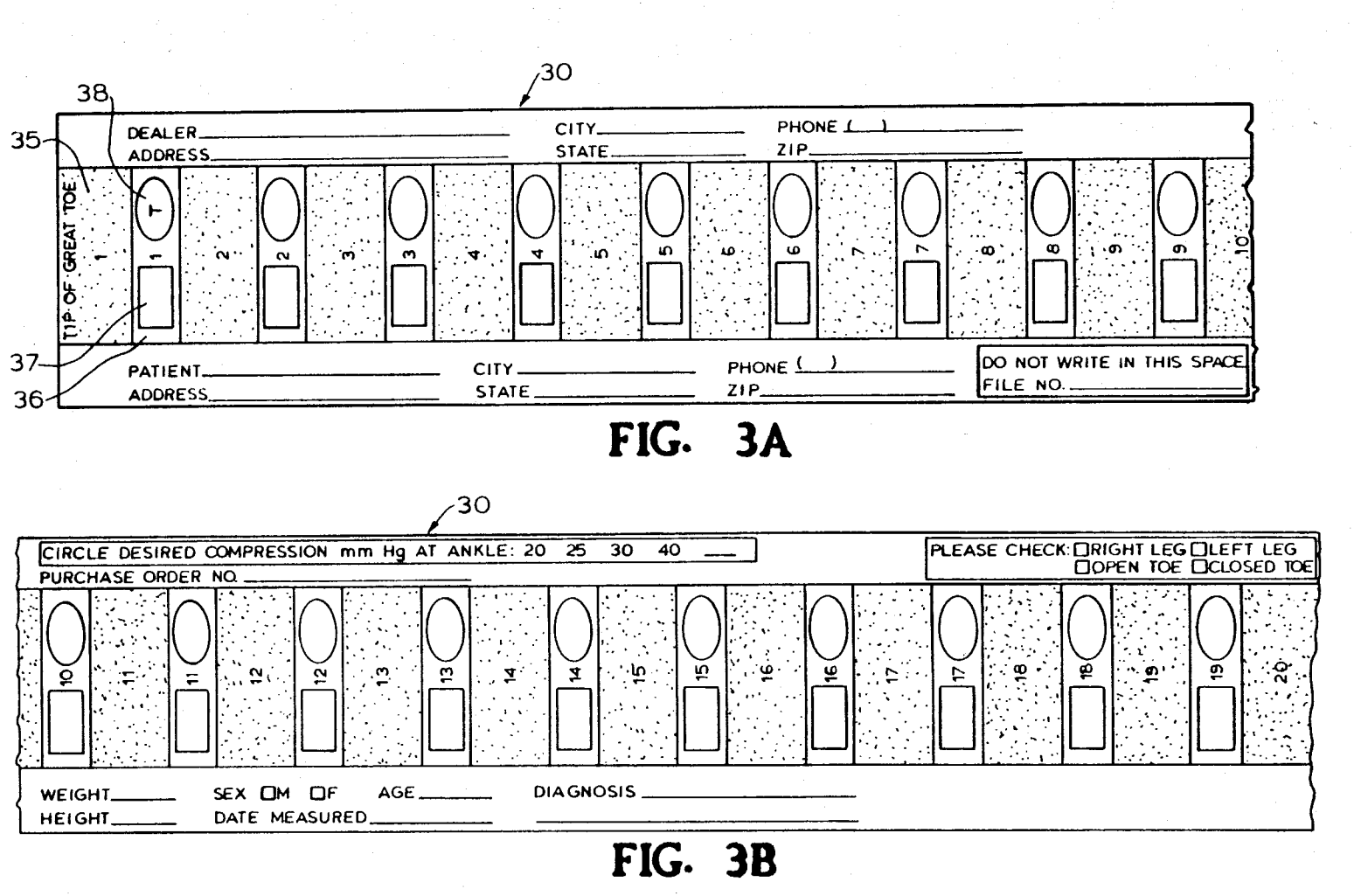
Figures 3C, 3D:
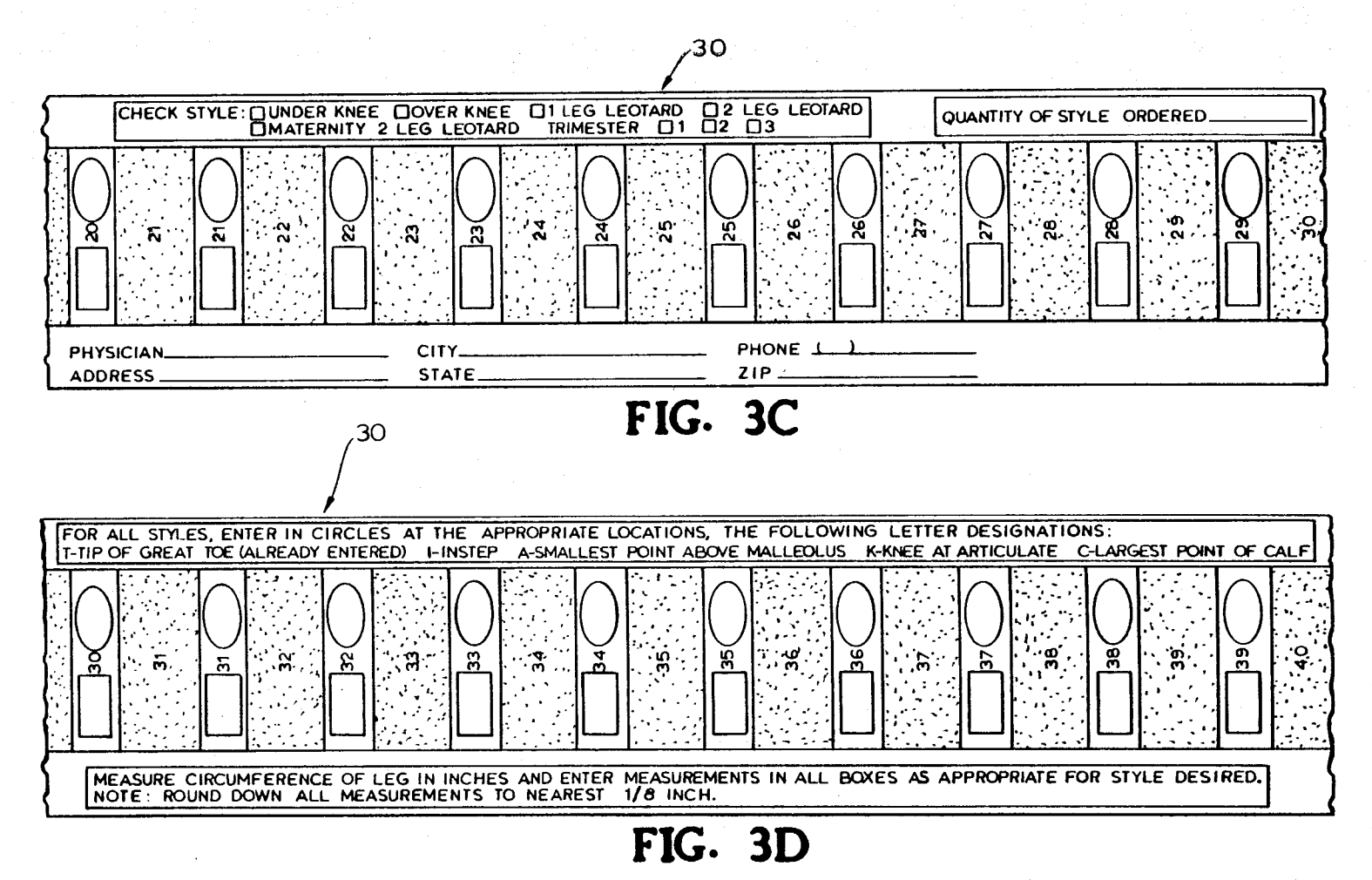
Figure 3E:
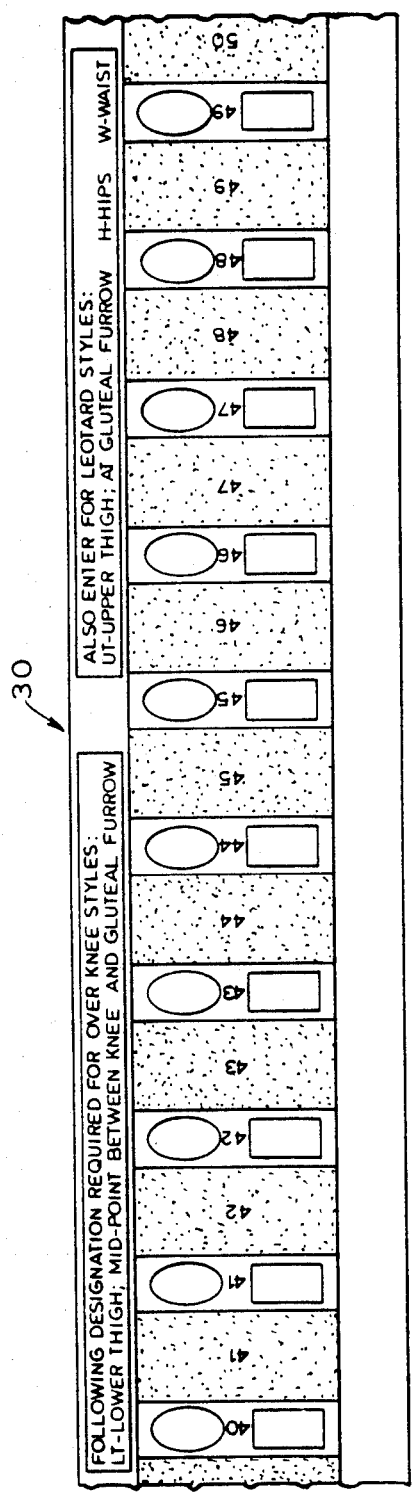
Figure 3F:
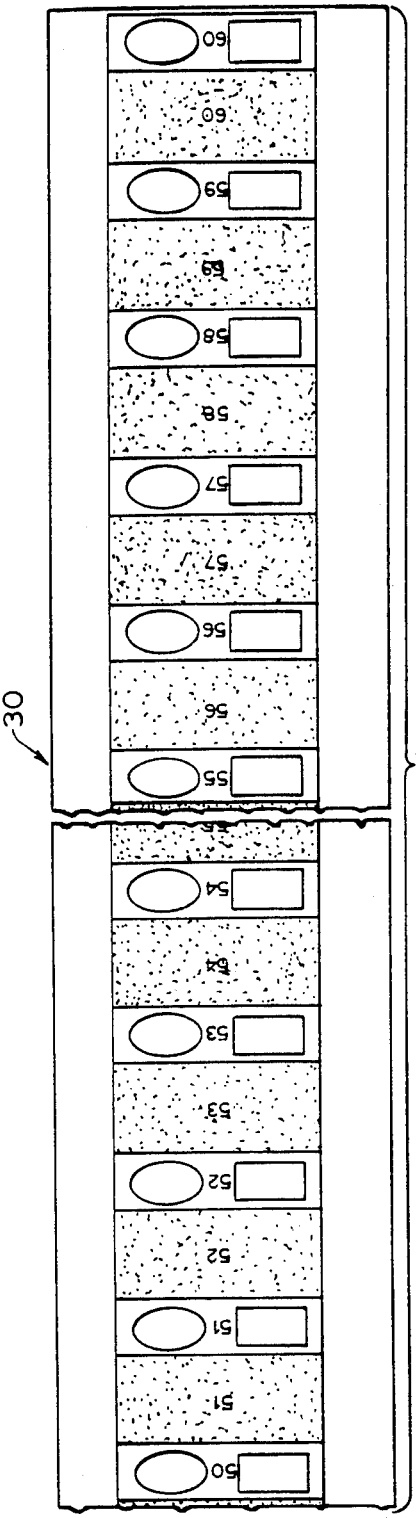

As further illustrated in FIGS. 3A-3F, it will also be noted that tape 30 on its face has a series of printed numbers 1-60 with each number being printed twice. The number is first printed in a shaded box outline, e.g., gray colored box 35 having the number 1 (FIG. 3A), and following this in the lengthwise direction of the tape, the same number is repeated in another smaller, unshaded box outline, e.g., box 36 (FIG. 3A), also having the number 1. The small box outlines are spaced apart by uniform intervals and in the illustrated example are on one inch centers. In each of the smaller box outlines, it will also be noted that there are printed respective rectangular and elliptical outlines, e.g., outlines 37, 38 (FIG. 3A). The numbers start at the toe end and increase toward the thigh end of the tape 30. As later explained, the rectangular outlines 37 are used for entering dimensions taken and the elliptical outlines are used for entering the respective locations of those body locations or control points corresponding for example to the tip of toe, T (FIGS. 1 and 7), and the like, with the letter T, at inch point 1, being preprinted as seen in FIG. 3A for establishing a starting position as later explained.

It has also been found desirable to preprint in the margins of tape 30 certain information to be filled in as later discussed and as further illustrated in FIGS. 3A-3F.

Figure 5:
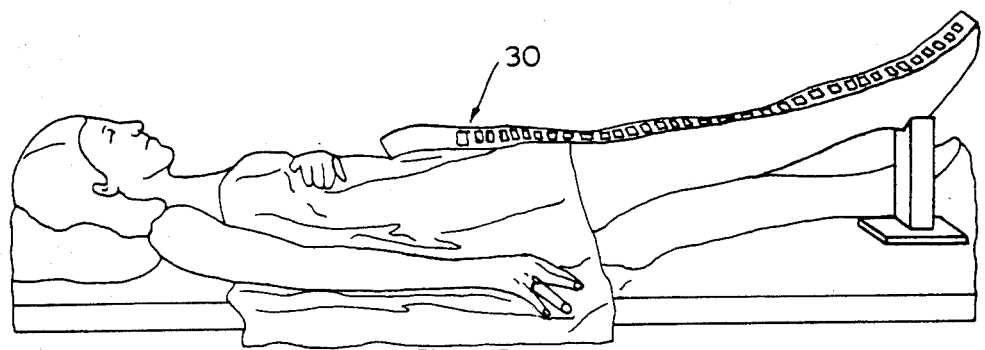
FIG. 5 is a pictorial view of a supine patient in the posture in which measurements are taken to produce the product of the invention.

The patient is measured in a supine position as illustrated in FIG. 5 and if hospitalized should be measured in bed before arising in the morning. If this is not possible, the patient should lie at rest in the supine position, with legs slightly elevated for thirty minutes to one hour prior to measurement. Constricting garments should be removed to permit any excess venous buildup in the legs to adequately dissipate.

While the patient is resting preparatory to being measured, the information data to be filled in as illustrated in FIGS. 3A-3F can be completed such as the dealer's name and address, the patient's name and address, the amount of compression, expressed in millimeters of mercury, desired at the ankle in the stocking, stockings or leotards being ordered, the purchase order number, the patient's weight, height, sex, and age and the date on which the measurement is being taken. A brief synopsis of the patient's diagnosis may also be entered with an indication of which leg is being measured, i.e., right or left. If the patient is being measured for a two-leg leotard, for example, a separate information tape 30 will be required for each leg. An indication can also be made as to whether the stocking or leotards being ordered are to be open toe or closed toe, the physician's name and address, the style of garment being ordered and if the patient is pregnant the current stage of pregnancy. Once the foregoing information has been entered on tape 30 and the patient has been positioned as illustrated in FIG. 5, the actual measuring operation can commence.

To initiate the measuring operation, the previously-mentioned adhesive cover strip 32 (FIG. 4) is removed from tape 30 and the patient's foot is positioned at a right angle to the leg so that the toes point up. The end of tape 30 marked "Tip Of Great Toe" (FIG. 3A) is placed so that it is even with the tip of the patient's great toe and is pressed so that the adhesive 31 on the back of tape 30 (FIG. 4) sticks to the toe surface, following which the remaining length of tape 30 is adhered by adhesive strip 31 to the full length of the patient's leg, i.e., up the foot to the ankle, up the shin, over the knee and up the thigh to the full extent of that portion of tape 30 to be used as best seen in FIG. 5.

Figure 6:
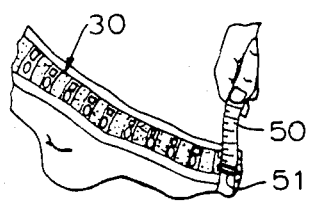
FIG. 6 is a fragmentary pictorial view of a lower foot measurement being taken.
Figure 7:
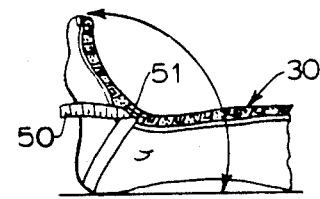
FIG. 7 is a fragmentary pictorial view of an instep measurement being taken.

The measuring tape 50 used for taking measurements should preferably be of the type having a loop 51 as illustrated in FIGS. 6-7. The first measurement is taken by placing an end loop of tape 50 over the end of the patient's foot, as in FIG. 6, so that the measuring tape 50 covers the number 1 gray box, i.e., relatively large gray outline box 35 on tape 30, as in FIG. 3A, immediately adjacent the legend "Tip of Great Toe". With the measuring tape 50 snug but not tight, the correct measurement is taken at the point at which the measuring tape doubles over the top of the loop 51 and is entered in the corresponding smaller size rectangular box 37. A first measurement of 8.5 inches at inch point 1 is indicated by way of example in FIG. 8. The letter designations shown in FIGS. 1 and 2 referring to the control measurement points, i.e., T, I, A, C, K, LT, UT, H, and W, are entered in the appropriate elliptical outline box at the appropriate locations as these control or reference measurements are taken. The letter "T" is preprinted in the elliptical outline 38. Measurements are also taken at each inch point between reference points and are recorded (now shown in FIG. 8) on information tape 30.

After taking the measurement corresponding to reference point T, the next reference measurement point corresponds to the letter "I" for the instep measurement. The instep measurement is taken, as illustrated in FIG. 7, by placing the measuring tape 50 on the particular information tape 30 shaded outline box 52 (FIG. 8) which is located closest to the bend of the foot where the foot starts into the ankle. The measuring tape is looped around the ball of the heel as further illustrated in FIG. 7 and the resultant measurement is recorded in the corresponding rectangular box outline 53 (FIG. 8) with a representative measurement 14.5 inches at inch location 7 being indicated in FIG. 8. In a similar manner, other control reference measurements are made at the following points:

A—Smallest point above malleolus.
C—Largest point of calf.
K—Knee at articulate.
LT—Lower thigh at the midpoint between the knee and gluteal furrow.
UT—Upper thigh at the gluteal furrow.
H—Hips.
W—Waist.

Figure 8:
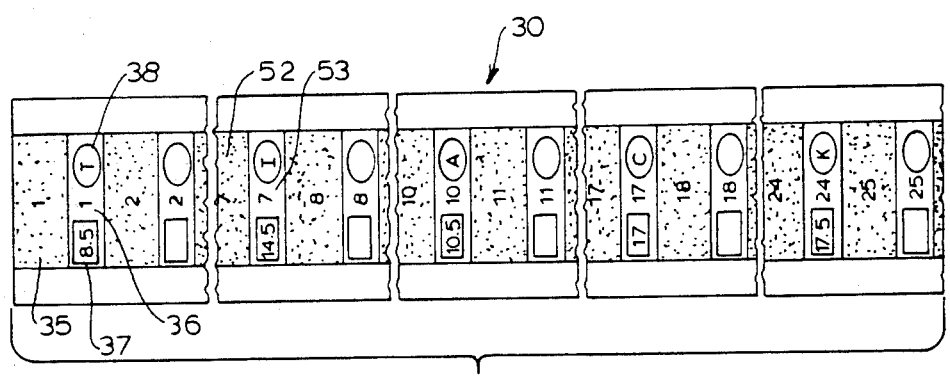
FIG. 8 is a fragmentary plan view of a portion of the measuring information tape shown in FIGS. 3A–3F with typical reference location measurements recorded thereon.

At each of the above reference points a measurement will be taken at the corresponding inch mark and will be entered in the appropriate small rectangular outline box as well as the appropriate letter or letters in the appropriate elliptical-shaped outline box as further illustrated in FIG. 8. Measurements other than at reference points are entered in the appropriate small rectangular outline box. It may also be noted that some styles of stockings do not require measurement of the entire length of the leg. For example, for an under-the-knee style of stocking (FIG. 22), the measurement can terminate at a point one inch below the bend of the knee. For an over-the-knee style stocking (FIG. 23), the LT (Lower Thigh) measurement will be the top measurement. For leotard styles (FIG. 25), the top measurement will be the W (Waist) measurement.

Figure 10A:
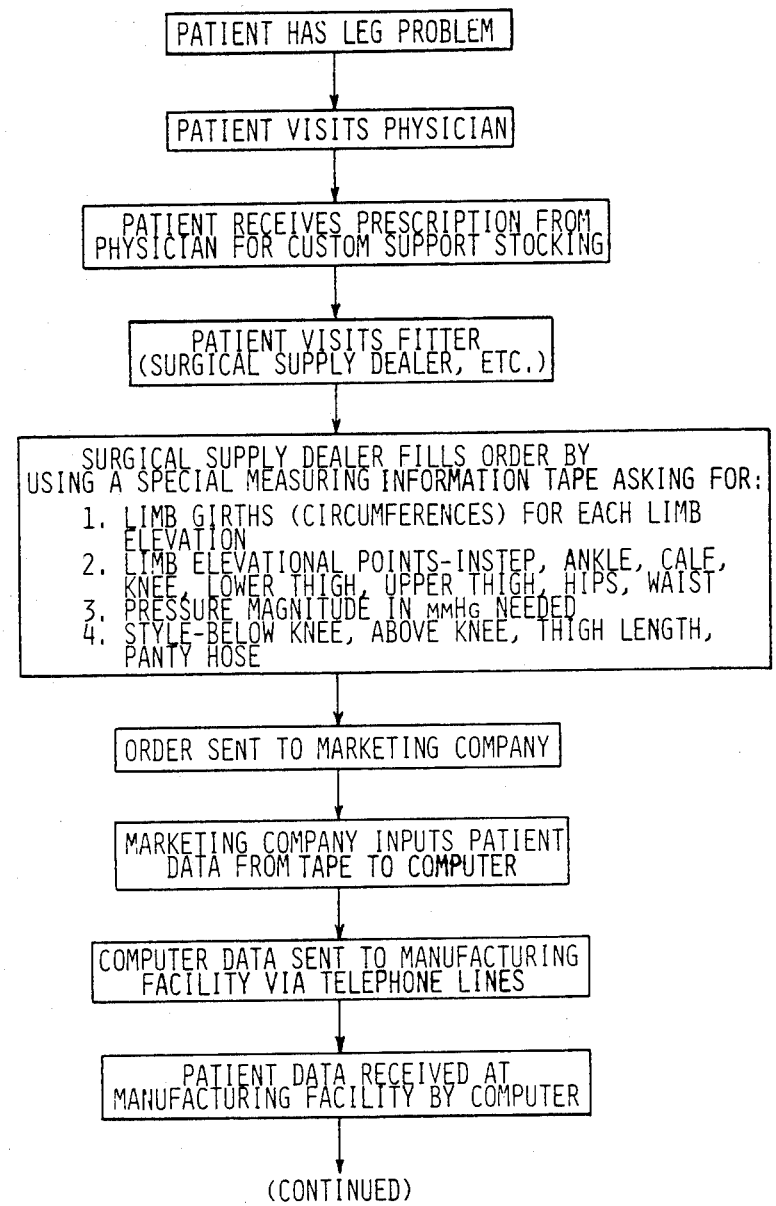
FIGS. 10A, 10B and 10C make up a composite flow diagram of the basic steps associated with a method for producing the product of the invention.

After the measuring operation has been completed on the patient's leg or legs for the particular style of stocking being ordered, the information tape 30 is removed from the patient's leg and folded so as to cover the adhesive backing material 31 (FIG. 4) and with continued folding as may be necessary to fit the complete tape 30 into an appropriate mailing envelope for mailing to the source of manufacture or to a point at which the patient information can be relayed by telephone or other form of communication to the source of manufacture as illustrated in FIG. 10A. When received at the source of manufacture, such information is preferably received in a form in which it can be immediately stored in memory as part of the control information for controlling the circular knitting machine which will be used to knit the particular customized stocking product of the invention according to the specific patient's prescription and needs.

As previously mentioned, the circular knitting machine being used by way of example on which the compressive stocking product of the invention is to be knit has two variable functions which determine compressive pressure and circumference, namely, cylinder height and the rubber feed speed. The terminology "rubber feed" is typically used to mean the mechanism for feeding the elastomeric threads whether in the nature of rubber, Spandex, or the like. These functions are controlled by means of later-explained computer-controlled electromechanical air cylinder-actuated racking devices (FIGS. 16–21) with the cylinder height having in the example used for illustration twelve possible positions and the rubber feed in the same example having forty possible speed positions so as to produce at one extreme a relatively loose fabric with low compression as in FIG. 13 or at the other extreme a relatively tight fabric with high compression as in FIG. 14 as well as graduated variations thereof. While in the illustrative invention product construction shown in FIG. 13, one rubber, e.g., Spandex, thread is knit in and another rubber thread is laid in as illustrated, those skilled in the art will readily appreciate that there are numerous other constructions suited to the invention product.

In the example chosen for illustrating how the invention product may be made, the twelve cylinder heights and forty rubber feed speeds thus allow for the possibility for 480 different combinations of machine settings. Each possible combination of machine settings, to the extent practical, is used to produce a test sample of fabric. In some instances, it has not been practical to knit a sample because of machine limitations related to the particular combination of machine settings. In any event, except for those instances in which the combination of machine settings were impractical to use for knitting the test sample, all of the possible 480 separate samples of fabric were knit and tested to derive the size and pressure information used in conjunction with a software program to decide and select the specific machine settings, i.e., cylinder height and rubber feed speed, to be used in various portions of the stocking product of the invention to be knit as further illustrated in FIGS. 10B and 11.

The fabric samples as well as the compressive stocking product of the invention being used by way of example were all knit on a multi-feed circular knitting hosiery machine with one elastic thread lay-in feed and using a 3¾ inch diameter cylinder. It has been found that the majority of patients in need of a compressive-type stocking will have measured circumferences falling within a range of 5.5 inches minimum to 49 inches maximum. With this limitation in mind, the sample fabric data base was developed with the further objective of being able to knit fabric exhibiting a sufficient number of different stretched circumferences at ⅛ inch increments to meet the full range of patient limb sizes and compression needs contemplated to be experienced in making the stocking products of the invention. Considering that in various portions of the compressive stocking product the stretched circumference may be held at some fixed value for some number of courses exceeding ⅛ inch in width, the invention data base was built up with the choice of being able to obtain 348 different possible stretched circumferences between a minimum of 5.5 inches and a maximum of 49 inches.

Figure 9:
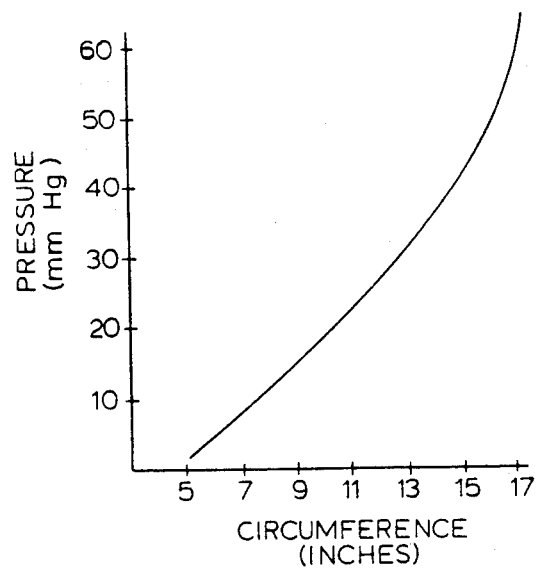
FIG. 9 is a typical modulus of elasticity curve as obtained from measuring a sample fabric tube for establishing a data base to produce the product of the invention.

The mentioned fabric samples after being fabricated were tested for pressure using a tensile testing device and the test on each sample was performed at circumferences which varied from the sample's limp width up to its dead stretch. The "reconstruction square" technique was employed, in which a 2"×2" square was stretched to simulate an actual wear condition. Each sample was tested for the pressure provided at ten intermediate, equally-spaced stretched circumferences between the limp width and the dead stretch. The ten intermediate test positions plus the limp width and dead stretch positions thus provided twelve different circumference test points for each sample. The twelve test points were then used to generate a modulus of elasticity curve for that particular sample. An example of this type of curve is shown in FIG. 9.

Figure 11:
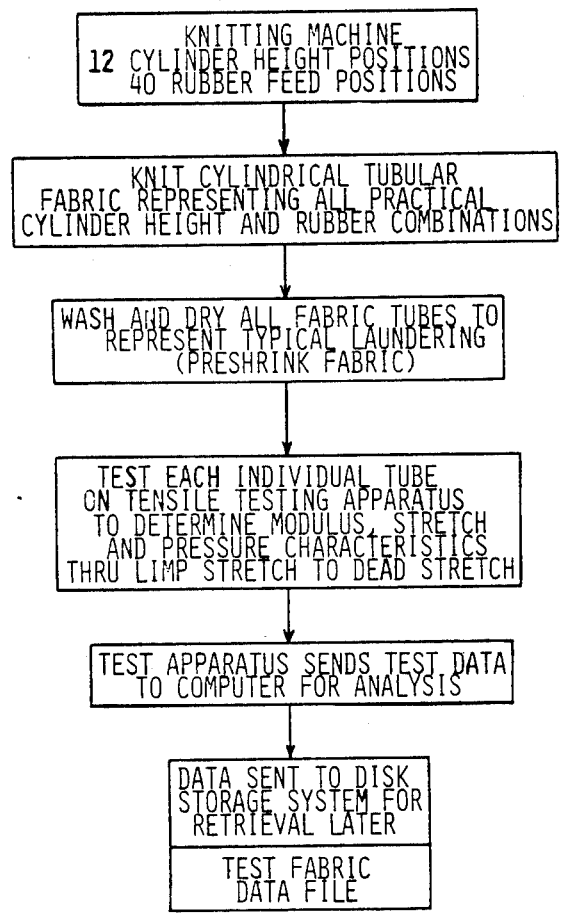
FIG. 11 is a flow diagram indicating the manner in which a data bank is established for providing a large number of possible stocking size and compression possibilities related to specific combinations of cylinder height and rubber feed positions.

The testing of the twelve data points by the tensile tester was monitored by computer, as diagrammatically illustrated in FIG. 11, with a statistical analysis program stretched circumference of 13.375 inches. Each pressure reflected in the example table was taken from a different sample. For example, at rubber feed setting 5, cylinder height setting 4, the indicated pressure of 39.9 was obtained, for example, from one of the 480 samples. Such a circumference table was prepared for each of the 348 stretched circumferences.

CIRCUMFERENCE = 13.375 Inches
Pressure in MM-HG as a Function of Machine Setting
Smoothed Pressure-Circumference Grid

| | | CYLINDER HEIGHT | | | | | | | | |
|---|---|---|---|---|---|---|---|---|---|---|
| | | 1 | 2 | 3 | 4 | ... | 9 | 10 | 11 | 12 |
| RUBBER | 1 | 0.0 | 0.0 | 0.0 | 0.0 | ... | 0.0 | 0.0 | 0.0 | 0.0 |
| | 2 | 0.0 | 0.0 | 0.0 | 0.0 | ... | 0.0 | 0.0 | 0.0 | 0.0 |
| | 3 | 0.0 | 0.0 | 42.4 | 40.5 | ... | 30.7 | 28.8 | 26.9 | 0.0 |
| | 4 | 0.0 | 0.0 | 41.7 | 39.7 | ... | 30.0 | 28.1 | 26.1 | 0.0 |
| | 5 | 44.8 | 42.9 | 40.9 | 39.9 | ... | 29.3 | 27.3 | 25.4 | 23.4 |
| | 6 | 44.1 | 42.1 | 40.2 | 38.3 | ... | 28.5 | 26.6 | 24.6 | 22.7 |
| | 7 | 43.4 | 41.4 | 39.5 | 37.5 | ... | 27.8 | 25.8 | 23.9 | 22.0 |
| | 8 | 42.6 | 40.7 | 38.7 | 36.8 | ... | 27.1 | 25.1 | 23.2 | 21.2 |
| | 9 | 41.9 | 39.9 | 38.0 | 36.0 | ... | 26.3 | 24.4 | 22.4 | 20.5 |
| | 10 | 41.1 | 39.2 | 37.2 | 35.3 | ... | 25.6 | 23.6 | 21.7 | 19.7 |
| | . | | | | | . | | | | |
| FEED | 33 | 24.1 | 22.2 | 20.3 | 18.3 | ... | 8.6 | 6.6 | 4.7 | 2.7 |
| | 34 | 23.4 | 21.5 | 19.5 | 17.6 | ... | 7.8 | 5.9 | 4.0 | 2.0 |
| | 35 | 22.7 | 20.7 | 18.8 | 16.8 | ... | 7.1 | 5.2 | 3.2 | 1.3 |
| | 36 | 0.0 | 20.0 | 18.0 | 16.1 | ... | 6.4 | 4.4 | 2.5 | 0.5 |
| | 37 | 0.0 | 19.2 | 17.3 | 15.4 | ... | 5.6 | 3.7 | 1.7 | 0.0 |
| | 38 | 0.0 | 18.5 | 16.6 | 14.6 | ... | 4.9 | 2.9 | 0.0 | 0.0 |
| | 39 | 0.0 | 0.0 | 15.7 | 13.8 | ... | 4.2 | 2.2 | 0.0 | 0.0 |
| | 40 | 0.0 | 0.0 | 15.1 | 13.1 | ... | 0.0 | 0.0 | 0.0 | 0.0 | to provide a fifth-degree polynomial equation with pressure as the dependent variable and circumference as the independent variable and of the form $$y = c_0 + c_1 x + c_2 x^2 + c_3 x^3 + c_4 x^4 + c_5 x^5$$

where y is the pressure, $c_n$ are constants, and $x^n$ are powers of x, where x is the circumference, and n ranges from 0 to 5. This equation allows the collected data to be stored in a highly condensed form and also allows a prediction of the pressure at any point within the stretch capability of the test sample. The twelve circumference test points with their corresponding pressures thus comprise 24 data variables for each sample. The fifth-degree equation allows the same information to be stored as a constant plus the multiplicative constants of the five powers of the circumference variable. The reduction of 24 pieces of data into six constants provides a substantial savings in the computer memory requirement as well as allowing an accurate prediction of the pressure at any point along the test sample modulus curve.

To determine the pressure at a given stretch circumference, from limp to dead stretch, for a specific test sample, the constants are called from the computer memory, the circumference and its required powers are input into the equation, the proper mathematical operations are performed, and the predicted pressure is obtained. It has been found that the predicted pressure based on the polynomial equation achieves an accuracy to within one part in 200 as compared to the actual pressure as determined on the tensile tester.

Once the polynomial pressure equations were developed for each of the different test samples, the equations were used to generate tables to indicate the pressure, expressed in millimeters of mercury, provided by a particular machine setting (i.e., the combination of cylinder height and rubber feed speed) at a particular circumference. An example table is shown as follows for a The pressure, in millimeters of mercury, that a particular combination of machine settings will provide can be determined from the table. No entry in the table indicates that no sample could be knit at that particular machine setting for the circumference on which the table is based. The minimum and maximum circumferences are restricted, respectively, to the test sample limp width and dead stretch. Some possible circumferences may be smaller than the sample limp width, while other circumferences are greater than the dead stretch of the sample. For these conditions, there will be no entry in the table. As previously mentioned, applicants have found that, with few exceptions, leg circumferences range from a minimum of 5.5 inches up to a maximum of 49 inches. These values are the limits placed on the circumference range of the type of compressive stocking made according to the invention. Pressure grid tables described above were generated for all values of circumference from 5.5 inches up to 49 inches in ⅛ inch increments, for a total of 348 separate pressure grid tables. These 348 separate pressure grid tables constitute the data from which the machine settings are selected to satisfy in the invention stocking product the physician's pressure and circumference criteria coordinated with the patient's actual physical measurements taken as previously explained.

As previously described, the physician or a designated assistant collects circumference data on a particular patient and determines the pressure profile he requires in the stocking. By pressure profile is meant the pressure exerted at the five leg locations or reference points indicated in FIGS. 1 and 2. The pressure exerted at these reference locations or points, other than the ankle, is referenced to the pressure at the patient's ankle and is given as a percentage of the ankle pressure. A pressure reference location other than the ankle could, of course, be selected. Based on clinical studies, a standard pressure profile has been determined which has been shown to be beneficial to a majority of the patients who use compression therapy. Referenced to the specified ankle pressure, the standard pressure profile is: calf (C), 80% ankle pressure; knee (K), 60% ankle pressure; lower thigh (LT), 40% ankle pressure; and upper thigh (UT), 20% ankle pressure. These percentages for the standard pressure profile are indicated in FIG. 2. By selecting the standard pressure profile, the physician only has to determine the ankle pressure for the patient's stocking and selects such ankle pressure based on the particular patient's need and customary pressure for such need and which is entered on tape 30 by circling the appropriate pressure indicated in FIG. 3B.

Figure 10B:
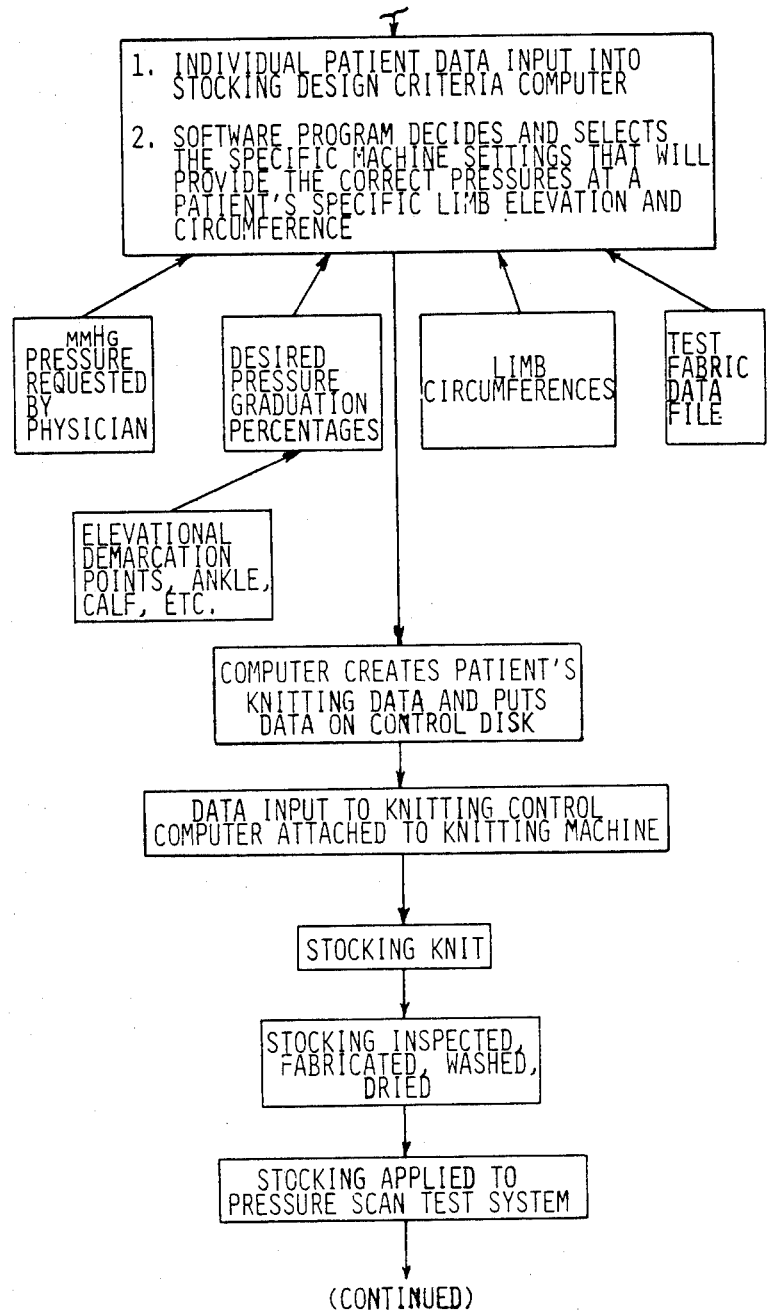
Figure 10C:
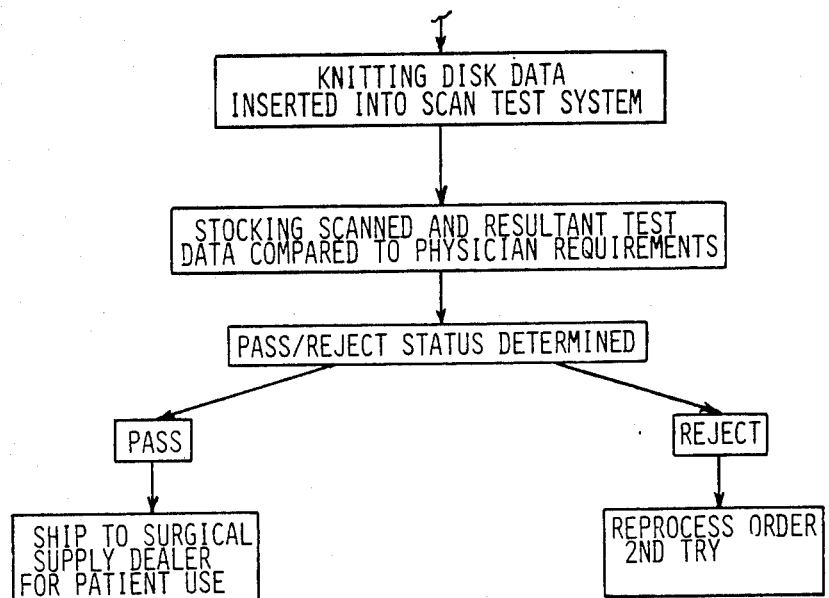
Figure 12:
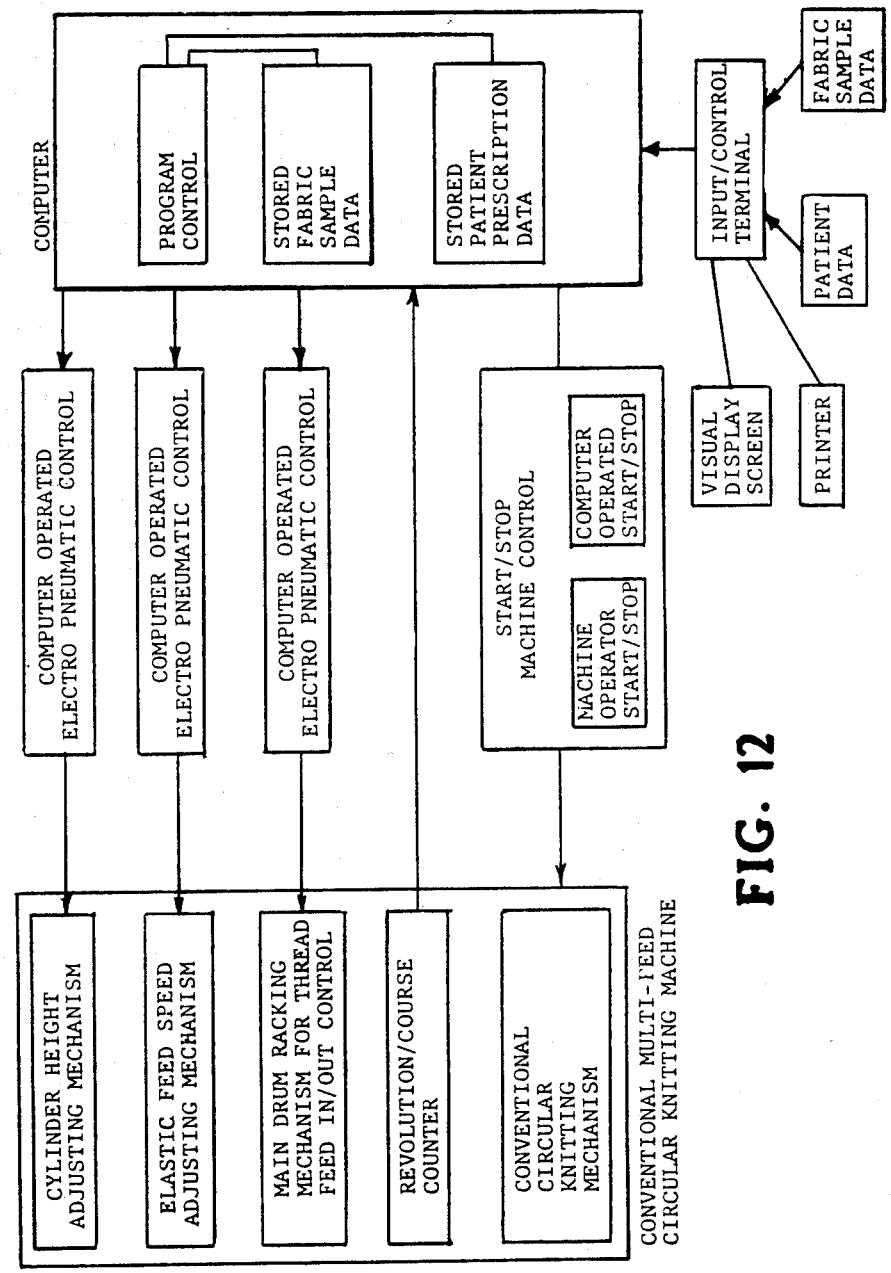
FIG. 12 is a schematic diagram of an overall system for producing the product of the invention.

Once the physician's data has been generated, it is entered into the computer memory for processing either through an operator terminal, through telephone wire communication, or the like as diagrammatically illustrated in FIGS. 10A, 10B and 12. Utilizing an appropriate software program, the computer uses the pressure profile to determine the pressure required at each leg circumference point. Such pressures are selected so as to provide a smooth, graduated transition, inch for inch, in pressure from the ankle, through each leg segment point, up to the gluteal furrow. Settings are selected so that insofar as is practical the compression changes in a linear relation between each pair of reference points allowing the overall change between the beginning and end reference points or locations to be non-linear. Both the computer and mechanical execution of changes in settings follow this objective at least in those portions of the stocking where the amount of compression is regarded as most critical for therapeutic purposes. For example, a good fit is all that is typically required in the waist portion. In addition, the pressures determined by the computer software also satisfy the physician-specified pressure profile. For each leg circumference point, a machine setting is determined which provides the required pressure and circumference. The computer accesses the pressure grid table for the circumference point under consideration and searches for the required pressure. Once this pressure is found, the machine settings which provide this pressure or the closest approximate pressure are read from the grid table and stored in memory. Typically, several combinations of machine settings will be found that provide the necessary pressure. Thus, an optimizing routine is built into the software such that the combination of machine settings which will provide the smoothest transition in machine setting change from each successive, previously-determined leg circumference point is selected. Preferably each of the 40 increments of yarn feed speed change results in a smaller change in pressure of a stocking than does each of the 12 increments of cylinder height change. Therefore, the optimizing routine maintains cylinder height constant for at least one inch as machine limitations will allow but changes yarn feed speed more frequently.

The process of machine setting determination progresses from the ankle, through each leg circumference point, at one-inch intervals, up to the gluteal furrow. Once these settings are determined and stored, the settings for the foot and, if applicable, the panty regions of the stocking are determined. The settings for these regions are based respectively on the size of the patient's foot and the circumference of his waist. The foot size or foot value placed in memory is determined by the I measurement (FIGS. 1 and 5) so as to provide for small, medium or large foot size. These machine settings are stored in the computer memory along with the machine settings for the graduated pressure, leg region of the stocking. All of the machine settings necessary to knit the customized support stocking of the invention are thus stored in the computer which is to be used for controlling the circular knitting machine during actual knitting of the desired compressive stocking being used by way of example.

As previously described, the computation of machine settings is made upwardly, i.e., from toe to welt, whereas the knitting is downwardly, i.e., from welt to toe. This allows the welts to be made on the machine.

The knitting of the invention stocking is a control operation during which the computer controls the cylinder position and rubber feed speed as a means of achieving the desired pressure profile, graduated pressures and circumference sizes corresponding to the physician-submitted data for the particular patient's stocking being knit. The knitting process begins at the top or waist region of the stocking, depending on the style being knit and proceeds through the graduated pressure leg region down to the tip of the foot. Throughout the knitting process, the computer controls the cylinder height position and the rubber feed speed of the knitting machine to provide a final product which meets the physician-specified criteria and offers a medically-correct, graduated pressure, support stocking for the patient.

While known programming procedures provide a variety of forms in which the knitting control information may be stored, analyzed, recovered from memory, selected, and the like, certain practical considerations are mentioned based on experience in making the stocking product of the invention. The program operates such that the stocking is typically started with the lowest possible cylinder height position, and the slowest possible rubber feed speed, i.e., the tight stitch positions. The program also calls for the cylinder height to be selected not more than once per inch whereas the rubber feed speed is selected each four revolutions of the knitting cylinder as determined by the revolution course counter mechanism shown in FIG. 15 and later described. In selecting machine settings, the computer program is organized so as to first select target pressures at the key points, i.e., locations A, C, K, LT, and UT. Pressures at the intervening inch points are next selected. Machine settings are determined keeping the cylinder height constant where possible and making only those changes in machine settings required to produce a smooth, substantially linear transition. Program commands can, of course, be delivered substantially instantaneously whereas mechanical execution of such commands takes time. In any event, changes in machine settings, whether for rubber feed, cylinder height, or both, are executed at evenly spaced intervals between the inch points. Thus, depending on the change in settings in going from one inch point to another inch point, the inch interval therebetween might be effectively divided by the computer once, twice or three times so that changes in the settings take place once, twice or three times in going form one inch point to the next. Execution of the mechanical commands are thus smoothed when implemented with the machine limitations programmed in. In general, it has been found desirable to minimize cylinder height changes and minimize rubber feed changes throughout execution of the knitting program for a particular stocking. The I, i.e., instep, value arbitrarily determines a foot value, i.e., small, medium, large, etc., which is used as a reference for knitting the foot portion of the stocking and which thereby controls the foot pressure. Other measurements could be employed to obtain a more specific and graduated pressure profile in the foot portion of the stocking. However, in actual practice, the obtaining of a graduated pressure profile is normally deemed more important from the ankle location upwardly. Where applicable, the W, waist measurement, determines the panty size. Waist pressure is normally not criticial. Thus, the waist or panty portion is primarily knit with the objective of obtaining a good fit.

Figure 27:
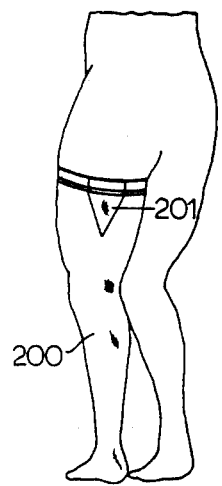
FIG. 27 illustrates a patient having an abnormally large upper thigh fitted with an alternative embodiment of the compressive stocking invention and having a triangular-shaped insert to produce a stocking for the patient's needs but beyond the knitting capability of the machine for such upper thigh circumference.
Figure 24:
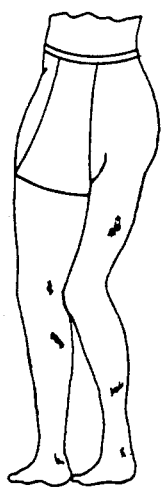
Figure 25:
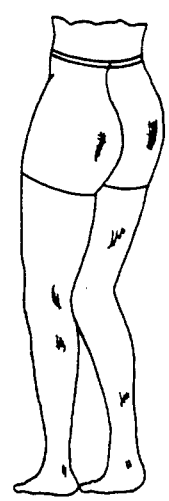
Figure 26:
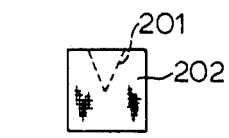
FIG. 26 schematically represents a rectangular-shaped test fabric sample from which a triangular insert, shown in dashed lines, is cut for installing in the stocking of FIG. 27.

Whatever size knitting machine is selected, such machine can only knit a fabric of some maximum stretched width. Therefore, where a patient's thigh measurement, for example, exceeds the machine's capability, the stocking 200 of the invention includes a triangular panel 201 in the upper thigh region as illustrated in FIG. 27. However, prior to cutting and sewing in such panel 201, a data file is made up by forming and tensile testing a range of rectangular-shaped fabric samples, made up with a wide range of cylinder height-rubber feed setting combinations, such as representative sample 202, shown in FIG. 26, from which the desired triangular panel 201 is cut. Such tests provide the compression characteristics of the fabric samples thereby enabling a computer determination of which sample is best suited so that after the triangular insert is seamed in placed as in FIG. 27, the desired compressive characteristics in the upper thigh region will be both known and achieved in practice in the finished product. In practice, a panty-type fabric having a knit in elastic yarn alternating with a non-elastic yarn is preferred for the inserts. Thus, a wide range of machine settings were employed to build up a range of panty hose fabric samples which after being tested provided a wide range of compression-circumferences combinations from which an optimized selection of a particular fabric sample can be designated by computer program from the test fabric data file. The end result is that even though the patient may have an unusually large upper thigh, and even though the circular knitting machine lacks the capability of knitting tubular fabric to accommodate to such patient in such region, the resulting stocking 200 with the insert 201, does meet the objective of achieving a predetermined pressure profile in such upper thigh region even though substantially larger than normal.

As previously mentioned and as schematically illustrated in FIG. 12, three mechanisms on the circular knitting machine are under program control in the method being used by way of example for knitting the invention stocking. These mechanisms include the rubber feed speed control, the in/out thread finger-drum racking control and the cylinder height control. Means are also provided whereby the knitting cylinder revolutions are counted and the count fed to the computer as electrical signals thereby enabling the course count to control the timing of operating the various program controlled mechanisms on the machine. Additionally, as shown in FIG. 12, means are provided whereby the computer can visually signal to the machine operator by a screen message when the knitting operation is ready to commence under program control. This mode of operation allows the operator to observe the screen visually for the appropriate message, e.g., "Now Ready To Start", or the like, so as to manually start the machine and also manually stop the machine on completion of the stocking. Alternatively, both stopping and starting of the machine as well as control of the machine during knitting can be performed through the computer under program control.

Since the general art of computers and programming of the type suited to the invention are known and since mechanisms for adjusting cylinder height and rubber feed speed and racking the drum to control thread finger positions are all old and well known, per se, as well as means for counting knitting cylinder revolutions and for starting and stopping the machine are all well known, the description will primarily direct itself to the general construction of these mechanisms and how they adapt for program control. The reader should also bear in mind that a conventional circular hosiery knitting machine is used by way of example and reference, the particular machine employed being equipped with two body yarn feeds, one lay-in elastic feed and a three and three-fourths inch cylinder.

The mechanism for revolution counting, i.e., course counting, is illustrated in FIG. 15 in which the main shaft 70, left clutch pinion 71 and right clutch pinion 72 are shown for reference. For purposes of counting each revolution of main shaft 70, corresponding to each rotation of the knitting cylinder and also to each course formed, there is provided a reflective surface 73 and a photo light source-detector 74 with connecting leads 75. As will be readily understood, detector 74 produces a pulse signal for each revolution and thus provides a means for counting the number of cylinder revolutions and courses knit and developing processible signals related thereto.

The elastic or so-called rubber feed speed control is somewhat schematically illustrated in FIGS. 16-18 in which thread 78 feeds between supply spool 80 and a driven roll 81. Thread 78 after leaving roll 81 is fed through a suitable guide or guides 82 and through a feed finger 84 to the needle circle 83. Roll 81 is mounted on driven shaft 85 which in turn is driven by a rubber tired wheel 86. Wheel 86 is loaded by compression spring 88 and has a suitable slidable, spline connection, not shown, to shaft 85 such that wheel 86 can both revolve with and slide lengthwise of shaft 85. Wheel 86 is in turn held in constant contact with a drive disc 90 driven at a constant speed off the main drive shaft by a drive shaft 91. Rubber feed speed is effectively controlled by controlling the radial position of wheel 86 with respect to disc 90. Thus, the further wheel 86 moves out from the center of disc 90, the faster wheel 86 turns and thus the faster drive roll 81 turns whereby to achieve a faster rubber speed. However, as wheel 86 moves closer to the center of disc 90, the rubber feed speed reduces and reaches a minimum when wheel 86 is centered over the center of disc 90.

A choice of 40 rubber speeds is provided by means of a bidirectional racking gear set 100 made up of gears 105, 106 each having 40 teeth and thus 40 possible positions. The gear set 100 is positioned bidirectionally by means of air solenoids 101, 102 controlled by a respective pair of electrically-controlled solenoid valves 103, 104 connected through a suitable controller 108 to the computer 110. Racking of gear set 100 bidirectionally causes the associated linear lobe cam 115 secured to gear set 100 to move in equal, corresponding bidirectional rotational increments and thereby raise and lower cam follower arm 120 accordingly. Use of a linear lobe cam facilitates use of program control to obtain uniform mechanical responses to computer commands and thus a smooth mechanical transition from change to change which reflects itself in the improved product of the invention. Arm 120 is connected to and positions rod 121 and in turn a bell crank arrangement comprising arms 126, 127. Motion of arm 127 back and forth thus causes wheel 86 to move in and out on disc 90 and thereby control the speed at which the elastic thread 78 is fed to the needles during those portions of the stocking in which elastic thread is employed for its desired compressive and therapeutic effect.

In operation the desired elastic thread feed is selected by the computer program for each portion of the stocking where elastic thread is used in conjunction with a selected cylinder height position for the same portion so as to obtain the desired circumference and pressure for that particular portion of the stocking. As the knitting operation proceeds through the various portions of the stocking, other rubber feed speed-cylinder height combinations are automatically fed to the controller 108 under program control for knitting the various portions of the stocking comprising the entire stocking construction. Selection of the rubber feed speed is thus effectively accomplished by selectively energizing either air cylinder 101 or air cylinder 102 according to whether rubber feed speed is to be reduced or increased. Computer 110 through programmed instructions, electrically signals either electrical solenoid valve 103 or 104 to achieve the desired rubber feed speed change.

As another aspect of operating the type hosiery machine being used by way of example for knitting the invention stocking, it is necessary to perform what is called racking the main drum which effectively means indexing the main drum to control the relative positions of certain of the knitting mechanisms including the thread feed fingers according to the portion of the stocking being knit. This racking or indexing operation is coordinated with forming the welt, leg, ankle and toe portions of the stocking with conventional reciprocating and other knitting mechanisms controlled off the main drum. In some instances, conventional practice requires that there be a so-called half rack or half throw of the main drum whereas in other cases it is desirable according to conventional knitting practice to have a full rack or full throw of the main drum for effecting a change in position of the main drum and thereby effect a particular change in the conventional knitting machine control mechanisms. The manner in which the main drum is racked by controlling the lifting and lowering of a pawl is explained in the book "Principles of Knitting" by William E. Shinn, 3rd Edition, 1957, published by Clark Publishing Company of Charlotte, N.C. With this background in mind, FIG. 19 schematically illustrates programmed controlled half rack and full rack indexing of the main drum. In FIG. 19, there is shown for reference a portion of the base of the clutch shipper fork 140, the clutch shipper shaft 141, the ratchet pawl lifter plate 142, the horizontal raising rod 143, and a modified somewhat lengthened ratchet pawl lifter 145. A frame support member 146 mounts an air solenoid 147 which, when energized, raises the ratchet pawl lifter 145 sufficient to accomplish a half rack or half throw of the main drum, not shown, through the clutch shipper shaft 141. Frame member 146 also mounts a second air solenoid 148 which when energized is arranged to raise the ratchet pawl lifter 145 in a longer stroke so as to accomplish a full rack or full throw of the main drum through clutch shipper shaft 141. As further illustrated in FIG. 19 the respective air solenoids 147, 148 are controlled through electrically operated solenoid valves 150, 151 connected to a suitable controller 152 which in turn is connected to the computer 110. For those familiar with the conventional racking operation of the type hosiery machine being used by way of example, it can be seen that by establishing control pulses under program control, such pulses fed from computer 110 through controller 152 to the respective electrical solenoid valves 150, 151 enable the main drum to be selectively racked either in a half rack or full rack according to the program requirements associated with the particular stocking being knit. The description next refers to the mechanism and control system associated with controlling the cylinder height as a means of controlling the stitch length and thereby, in conjunction with the rubber feed speed control, controlling the compressive effect of the stocking product of the invention.

Stitch length and consequently the compressive effect of the stocking fabric may be controlled on the type circular knitting machine being used by way of example by various means including raising and lowering the stitch cams or raising and lowering the cylinder with respect to the cams. In either case the known mechanical mechanisms have been previously used to selectively provide a relatively loose stitch as in FIG. 13 or a relatively tight stitch as in FIG. 14. The apparatus and method being used for explaining how the invention stocking product is made brings to this known practice, the practice of enabling program control to establish the tightness of the stitch and in the present example is based on using cylinder height control as the stitch length control. The mechanism and control apparatus for this example is schematically illustrated in FIGS. 20-21.

Figure 13:
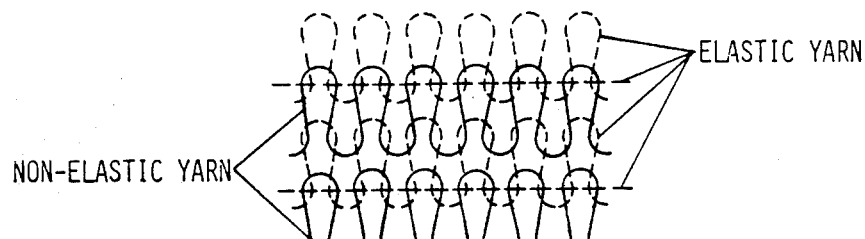
FIG. 13 is a fabric stitch diagram for a relatively low compression fabric.
Figure 14:
FIG. 14 is a fabric stitch diagram for a relatively high compression fabric.
Figure 21:
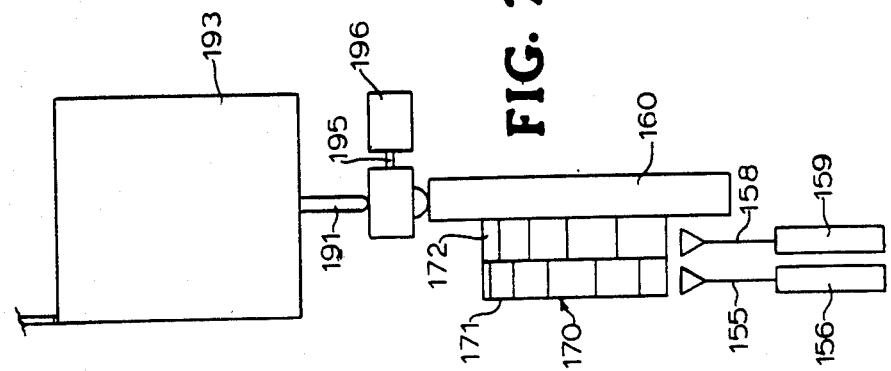
FIG. 21 is a front and somewhat schematic elevation view of the cylinder height control seen in FIG. 20.
Figure 20:
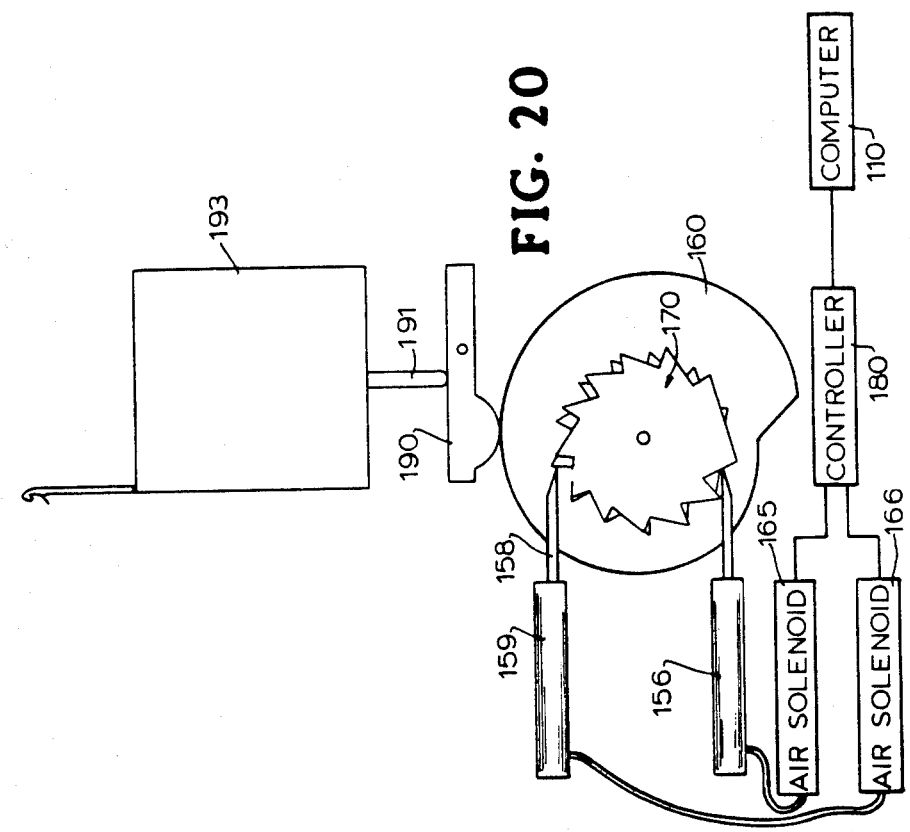
FIG. 20 is a side and somewhat schematic elevation view of the cylinder height control used in a knitting machine for making the product of the invention.
Figure 22:
FIGS. 22, 23, 24 and 25 illustrate respectively below-knee-type, above-knee-type, one-leg-leotard-type and leotard-type compressive hosiery products of the type which can be made according to the invention.
Figure 23:
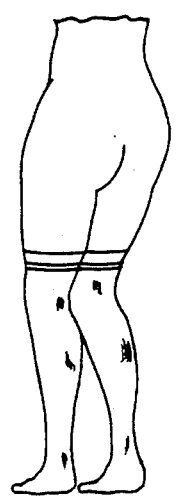

In FIGS. 20-21, there is shown a progressive linear lobe cam 160 secured to a gear set 170 comprising a pair of gears 171, 172, each having respective sets of 12 teeth corresponding to 12 cylinder height positions. As with the linear lobe cam 115 used for controlling the rubber feed speed, use of linear lobe cam 160 facilitates use of program control to obtain uniform mechanical responses to computer commands. Each mechanical change is thus in a predetermined amount and overall leads to a smooth mechanical transistion from change to change and substantially linear compression transistions in the invention product. Gear 171 is actuated by a pawl 155 controlled by an air cylinder 156 and gear 172 is actuated by a pawl 158 actuated by air cylinder 159. The air cylinders 156, 159 are controlled through respective electric air solenoid valves 165, 166 connected through a suitable controller 180 to computer 110. Lobe cam 160 is thus positioned in one direction or the other dependent on which of the two air cylinders 156, 159 are energized which is in turn dependent on which of the electrical solenoid control valves 165, 166 is energized through controller 180 by the selection program established by computer 110. Bidirectional positioning of lobe cam 160 controls positioning of follower arm 190 connected through linkage 191 so as to raise and lower cylinder 193. Arm 190 pivots on a shaft 195 mounted on a support 186 suitably fixed to the machine frame. Since cylinder height positioning as such has been previously known (see for example the book "Principles of Knitting" previously referred to) those skilled in the art will readily appreciate from the schematic illustration of FIGS. 20–21 and the brief description given how computer 110 controls the position of cylinder 193 under program control and thereby controls the looseness and tightness of the stitch as depicted in FIGS. 13–14 to obtain a selected pressure profile.

In summary, the improved product provides a tubular fabric product customized to a specific body contour and desired compression profile for such contour. Looked at broadly and considering the described insert embodiment of FIGS. 26–27, the invention also offers the possibility of such tubular goods being formed either from tubular fabric or from flat fabric having known circumferential compression characteristics when fabricated into tubular form. As specifically applied to the art of compressive stockings, the invention product brings to the art at least the following features not heretofore known:

1. A compressive stocking construction according to a specific patient's prescription.
2. An optimized and variable pressure profile in a compressive stocking.
3. A compressive stocking in which compression changes from one reference location to another are substantially linear.

While primarily intended to serve the needs of those patients requiring therapeutic compressive stockings, and the like, it is also recognized that the invention opens up the opportunity for broader application to other types of circular knit goods where circumference and/or pressure are critical characteristics. The desired pressure profile may be a graduated profile corresponding to some standard profile referenced to the ankle pressure as previously described. However, the invention also readily adapts to any other profile referenced to other body locations and graduated in percentages other than those described by way of example. Combinations of graduated and uniform pressures in different portions of the stocking product of the invention may also be achieved.

What is claimed is:

1. An elasticized knit-fabric seamless garment adapted to substantially fit an anatomic form such as a human limb and exhibiting throughout the length of some predetermined portion of such garment when fitted to said form at each of plural reference locations, such as at the ankle, calf, knee, lower and upper thigh locations on the leg, spaced apart by some plural number of uniform predetermined increments of lengthwise measurement which number may vary between selected successive reference locations, a predetermined amount of compression representing a known percentage of the compression at one of the reference locations and at locations between each pair of such reference locations predetermined amounts of compression graduated in a controlled amount such that in said predetermined portion a plurality of said reference locations are included and starting at a beginning reference location, e.g. the ankle, and ending at an end reference location, e.g. the upper thigh, the compression from each reference location to the next successive reference location throughout said predetermined portion changes in a substantially linear relation and providing an overall non-linear change between said beginning and end reference locations and exclusively linear changes between each pair of said reference locations and exclusively linear changes between each pair of said reference locations.

2. An elasticized knit-fabric garment as set forth in claim 1 wherein said garment comprises a tubular circular knit elasticized garment.

3. An elasticized knit fabric garment as set forth in claim 2 wherein said garment comprises a compressive stocking adapted to fit a leg upwardly from the ankle and the amount of compression asserted at each said reference location in the finished compressive stocking is substantially equal to some known percentage of the compression asserted at the ankle location thereof and said linear relation corresponds to each change from one said known percentage of compression at one reference location to the said known percentage of compression at the next said reference location.

4. An elasticized knit fabric garment as set forth in claim 2 including a panel insert joined so as to form a portion of said tubular fabric and having compression characteristics consistent with the compression characteristics of the remainder of said fabric.

* * * * *

UNITED STATES PATENT AND TRADEMARK OFFICE
CERTIFICATE OF CORRECTION

PATENT NO. : 4,502,301
DATED : March 5, 1985
INVENTOR(S) : Roger T. Swallow; William R. Jackson; Jack D. Pierce It is certified that error appears in the above—identified patent and that said Letters Patent is hereby corrected as shown below:

Col. 2, line 67, "heightrubber" should be --height-rubber--.

Col. 12, line 64, "form" should be --from--.

Col. 18, lines 22-23, delete "and exclusively linear changes between each pair of said reference locations".

Signed and Sealed this

Eighteenth Day of June 1985

[SEAL]

Attest:

DONALD J. QUIGG

Attesting Officer

Acting Commissioner of Patents and Trademarks